United States Patent [19]

Becker et al.

[11] 4,154,244
[45] May 15, 1979

[54] BALLOON-TYPE CATHETER

[75] Inventors: Lawrence F. Becker, Chicago; John J. Donohue, Vernon Hills; Dean G. Laurin, Lake Zurich; Henry M. Gajewski, Winnetka, all of Ill.

[73] Assignee: Baxter Travenol Laboratories, Inc., Deerfield, Ill.

[21] Appl. No.: 853,738

[22] Filed: Nov. 21, 1977

[51] Int. Cl.² .......................................... A61M 25/00
[52] U.S. Cl. ................................... 128/349 B; 156/294
[58] Field of Search ........ 128/349 B, 349 BV, 349 R, 128/348; 156/294

[56] References Cited

U.S. PATENT DOCUMENTS

| 3,503,399 | 3/1970 | Ettman et al. | 128/349 B |
| 3,528,869 | 9/1970 | Derewiuk | 128/349 B X |
| 3,889,685 | 6/1975 | Miller, Jr. et al. | 128/349 B X |
| 3,926,705 | 12/1975 | Todd | 128/349 B X |
| 3,982,544 | 9/1976 | Dyck | 128/349 B X |
| 4,026,296 | 5/1977 | Stoy et al. | 128/349 B |

FOREIGN PATENT DOCUMENTS

| 904138 | 7/1972 | Canada | 128/349 B |
| 2433959 | 7/1974 | Fed. Rep. of Germany | 128/349 B |
| 2454358 | 5/1075 | Fed. Rep. of Germany | 128/349 B |
| 1234037 | 6/1971 | United Kingdom | 128/349 B |
| 1313347 | 4/1973 | United Kingdom | 128/349 B |

Primary Examiner—E. H. Eickholt
Attorney, Agent, or Firm—Paul C. Flattery; John P. Kirby, Jr.; Garrettson Ellis

[57] ABSTRACT

A balloon-type catheter is disclosed having a catheter shank made of a block copolymer having thermoplastic rubber characteristics with a central block of ethylene-butylene copolymer and terminal blocks of polystyrene. The inflatable balloon member, and preferably the distal Y-member, of the catheter are made of an elastic composition which includes the same or a similar block copolymer, in the presence of polystyrene or equivalent material as a tackifying agent, polypropylene, and an oil-type plasticizer.

7 Claims, 2 Drawing Figures

BALLOON-TYPE CATHETER

BACKGROUND OF THE INVENTION

Balloon catheters are commonly used, particularly the Foley catheter which finds major use in uninary tract surgery. The catheter is inserted into the urethra until the catheter head extends into the bladder. Then a balloon adjacent the head is inflated to retain the catheter for usually a period of days. However, a catheter may be inserted for an indefinite period of time in chronic situations.

The early designs of balloon catheters were made of natural rubber latex. As is known, the latex causes a reaction in the tissues which are adjacent to it, which can be quite uncomfortable for the patient, and which is medically undesirable.

In more recent times, balloon catheters have been fabricated out of silicone rubber, or out of latex which is coated with a film of silicone rubber, to avoid the tissue reaction problem. However, these catheters are considerably more expensive than the latex catheters, and they share with the latex catheters the disadvantage that they are somewhat difficult to fabricate, because both latex and silicone rubber are generally not thermoplastic materials, and thus must be cured over a period of time in order to obtain the desired physical properties.

Another type of balloon catheter has a polyvinyl chloride tubular shank, attached to a natural rubber latex balloon, because of the unsuitability of vinyl as a balloon material. Thus, the latex balloon remains as an irritant. Also, vinyl catheters have exhibited an undesirable "feel" to the patient.

In accordance with this invention, a new catheter is provided which can exhibit an extremely low toxicity so that little or no irritation is felt by the patient. The balloon of the catheter of this invention exhibits particularly good elastomeric recovery, with low creep, so that there is little "pruning" upon deflation of the balloon, i.e. the formation of wrinkles in the balloon.

While the material of the catheter of this invention, on a cost basis, is similar to natural rubber latex and the like, it is as non-toxic as silicone rubber, thereby combining the advantages of the two types of catheters.

Also, as a further advantage, the tubular shaft of the catheter of this invention may be formed by simple extrusion, without a post cure time, since the material of the catheter may be thermoplastic, but also of a softening temperature which permits autoclaving of the catheter if desired.

Also, parts of the catheter may be thermoformed or injection molded as desired. The tubing of the catheter of this invention may be kink and collapse resistant upon aspiration and normal use, and it may be fabricated by heat sealing, without separate adhesives.

Also, the cost of fabrication of the catheters of this invention may be further reduced by the fact that scrap materials from the production of the catheter may be reused in molding or extrusion, since the material is of thermoplastic rather than of the thermoset type.

The catheters of this invention are also stable under radiation sterilization.

DESCRIPTION OF THE INVENTION

In accordance with this invention, a balloon type catheter is provided with a tubular shaft and an inflatable balloon member, carried by said catheter, said shank and balloon member each being made of elastic compositions which comprise: at least 40 percent by weight of a block copolymer having thermoplastic rubber characteristics with a central block of ethylene-butylene copolymer and terminal blocks of polystyrene; from 0 to 45 percent by weight of polypropylene; at least one of said shank and balloon member containing from 5 to 30 percent by weight of tackifying agent comprising a low molecular weight polystyrene; said elastic compositions being mixed with sufficient hydrophobic oil-type plasticizer to provide the desired physical properties to said shaft and balloon member, i.e. low modulus, softness and resistance to creep.

However, if the molecular weight of the block copolymer formulations is of an average of about 80,000 or less an adhesive or tackifying agent may not be needed to seal the parts together. Specifically, the block copolymers having thermoplastic rubber characteristics described above are commercially available under the trademark KRATON from the Shell Chemical Company, or SOLPRENE from the Phillips Petroleum Company. Other rubbery block copolymers which are available under these trademarks utilize a central block including butadiene or isoprene, rather than the ethylene butylene copolymer units preferably utilized herein. These substitute materials may be contemplated for use as equivalents to the ethylene-butylene copolymer block.

These block copolymer materials preferably have a Brookfield viscosity of 10 to 2000 cps. as a ten weight percent toluene solution, measured at 25° C. for the purposes of this invention. These materials exhibit the characteristics of a thermoplastic rubber, due to the combined effects of the central block of the molecule, which is typically a rubbery, polyolefin material, and the terminal blocks of thermoplastic polystyrene.

Mixtures of the above-described block copolymers of different molecular weight also may be desirable for use. An advantage of such mixtures is that a component of the mixture may include the block copolymer as described above with a molecular weight which is in itself too high to permit extrusion, with the extrudability being facilitated by a component of lower molecular weight block copolymer, to obtain an advantage in physical properties from the high molecular weight component (for example, a solution viscosity as calculated above of 1000 cps. The lower molecular weight components of the block copolymer described above may preferably have similar solution viscosities on the order of 20 to 100 cps.

Preferably, in the block copolymers described above, the central block of ethylene-butylene units may comprise 50 to 85 percent by weight of the copolymer molecule, while the terminal blocks of polystyrene or equivalent material comprise the balance of the compound.

This formulation used herein may also contain a titanium dioxide pigment or the like, for appropriate coloration of the catheter, as well as other desired additives such as a stabilizing agents, plasticizers such as mineral oil, and flow aid and hardener materials such as polypropylene.

Typically, a molded, branched connector such as a Y-site is attached at the distal end of the tubular shaft of the catheter. The branched connector may also be made of the elastic composition described above.

Either or both of the shaft and the balloon member (and the branched connector when used) desirably may contain from 5 to 30 percent by weight of tackifying agent such as low molecular weight polystyrene. When at least one of the formulations contains this material, it facilitates the adhesion of the balloon member and the Y-connector to the catheter shaft without the use of adhesive by heat sealing or molding the balloon member and connector in place on the shaft. The polystyrene material used may preferably be of a molecular weight, for example, of 1000 to 6000, as a tackifier.

Preferably up to 30 percent of the polypropylene may be used in the oil-extended compound, both as a flow aid and as a surface finish, depending on the molecular weight of the polypropylene. Generally, more polypropylene is needed as a flow or extrusion aid when the block copolymers used in this invention are of higher molecular weight. In particular, from about one to five weight percent of polypropylene having a melt flow of about 50 to 100, as tested under ASTM D1238-70, provides an improved, smooth surface finish. Also, crystalline polypropylene is believed to act as a diffusion barrier.

Figure 1:
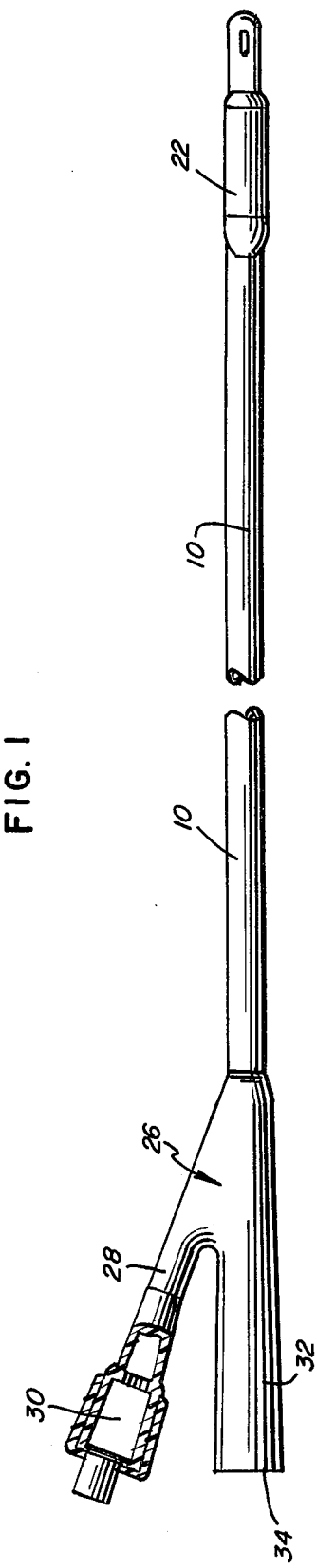
FIG. 1 is a plan view of a typical Foley catheter which may be manufactured in accordance with this invention.
Figure 2:
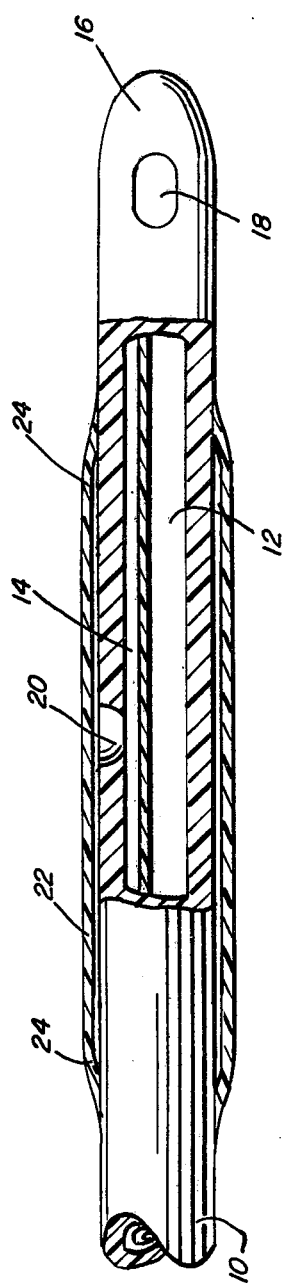
FIG. 2 is a detailed view of the catheter of FIG. 1, taken partly in section, showing the catheter balloon member adhered to the catheter shaft.

Referring to the drawings, the catheter of this invention is shown defining a double lumen tubular shaft 10 which may be extruded to define a drainage lumen 12 and an inflation lumen 14 in accordance with conventional technology. Tip member 16 may be conventionally thermoformed on the catheter so that drainage lumen 12 communicates through aperture 18 to the exterior, and inflation lumen 14 is closed off.

Aperture 20 is provided in the wall of shaft 10 to provide communication between the inflation lumen 14 and the exterior of shaft 10. Balloon 22, being a thin-walled tube, is sealed, for example by non-contact radiant heat source, at ends 24 to the outer wall of shaft 10 about aperture 20. Accordingly, when pressurized air or liquid is provided to inflate lumen 14, balloon 22 will expand.

Branched or Y-connector 26 comprises a pair of branching channels. Channel 28 is adapted to receive a pressure syringe, and communicates with the inflation lumen 14. Valve 30 is provided to receive the luer of a yringe and to allow it to pass to place pressurized fluid into the inflation lumen 14. Valve 30 is also adapted to retain that pressure when the syringe is withdrawn, and may be of conventional construction for a Foley catheter. Branched tube 32 is adapted to communicate with the catheter adapter of a urinary drainage bag or the like at its outer end 34, and communicates with drainage lumen 12 within catheter shaft 10.

The following examples are provided to illustrate specific examples of formulations which may be utilized in the catheter of this invention. These specific examples are for illustrative purposes only, and are not intended to limit the scope of the invention of this application, which is as defined in the claims below.

EXAMPLE 1

A material for formulating extruded shaft 10 of the catheter invention was prepared by mixing the following ingredients in a ribbon blender: 100 parts by weight of a block copolymer of ethylene butylene copolymer having terminal blocks of polystyrene (known as Kraton G1651—Brookfield viscosity as a 10 weight percent solution in toluene at 25° C.—1000 cps.; weight percent of the central block: 67 percent); and 40 parts by weight of polypropylene having a melt flow of 5 (ASTM D1238—70; Shell 5520). To this mixture was added 100 parts by weight of U.S.P. light grade white mineral oil, manufactured by Witco Chemical Company, Sonneborn Division, New York, New York; (viscosity at 100 degrees F. of 350 Saybolt seconds) as a plasticizer. To this formulation was also added about 0.03 to 0.07 percent by weight of an equal weight mixture of two stabilizers, one commercially available under the trademark Irganox 1010 by the Ciba-Geigy Company, and the other being dilauryl-thiodipropionate One hundred parts by weight of the following formulation were blended with one part by weight of a titanium dioxide pigment (Ti-Pure R-221, manufactured by E. I. DuPont de Nemours).

After mixing of this formulation, it was extruded at 350-400 degrees F. in a conventional extruder to form the double lumen catheter tube 10.

For the catheter of this invention, balloon member 20 was extruded and Y-connector 26 was conventionally molded out of a formulation containing the following ingredients:

(a) 65 percent by weight of a mixture of 100 parts by weight of the block copolymer described immediately above (Kraton G1651) and 85 parts by weight of the mineral oil described above;

(b) 17 percent by weight of a mixture comprising 100 parts by weight of an ethylene butylene block copolymer with polystyrene end blocks of lower molecular weight (Kraton G1650; Brookfield viscosity as a 10 percent toluene solution—60 cps. at 25 degrees C.; weight percent of the ethylene-butylene block: 70 percent); 51 parts of polypropylene having a melt flow of 12 according to ASTM D1238-70 (Shell 5820); 19 parts by weight of a copolymer of alphamethyl styrene and vinyl toluene (Piccotex 120, sold by Hercules Chemical Company); and 100 parts by weight of the mineral oil described previously.

(c) 15 percent by weight of a low molecular weight polystyrene having a ring and ball softening point of about 100 degrees C. (Piccolastic E100, sold by Hercules Chemical Company).

(d) 3 percent by weight of a high melting polypropylene (Tenite 4G7DP sold by Eastman Chemical Products, Inc.) having a melt flow of 60 according to ASTM D1238-70), as a surface finish improving agent.

To one hundred parts by weight of the above formulation was added one part of the titanium dioxide pigment described above. The mixture was thorougly mixed in a ribbon blender; the balloon 22 was heat sealed in position on shaft 10, while Y-connector 26 was molded on the catheter, both without adhesive. Tip 16 is thermoformed.

The formulation also contains from 0.03 to 0.07 percent by weight of the stabilizers described earlier.

EXAMPLE 2

Another catheter may be prepared by extruding shaft 10 out of a formulation of the following composition:

A. 60 percent by weight of a mixture of 100 parts by weight of Kraton G1651 (described above) and 85 parts by weight of the mineral oil described above.

B. 5 percent by weight of polypropylene having a melt flow of 60 under the test described above (Tenite 4G7DP).

C. 10 percent by weight of the low molecular weight polystyrene described above (Piccolastic E100).

D. 5 percent by weight of polypropylene having a melt flow of approximately 2 according to ASTM D-1238 (condition L).

E. 20 percent by weight of the mineral oil described above.

One hundred parts of this formulation were mixed with two parts of the titanium dioxide pigment described in Example 1, and blended for extrusion at 350 degrees to 400 degrees F. into the double lumen shaft 10 of the catheter of this invention.

The balloon 22 may, in this instance, be extruded from a formulation of the block copolymer of ethylene-butylene with polystyrene end blocks, in which the ethylene-butylene portion of the copolymer comprises about 70 percent by weight of the copolymer molecule, having a Brookfield viscosity at 25 degrees C. of 20 cps. using a 10 weight percent solution in toluene, and containing from 0.03 to 0.07 percent by weight of A0330 antioxidant (Kraton G1662). To this is added 40 percent by weight of the mineral oil described in Example 1 above. The composition is then blended.

One hundred parts by weight of this blended formulation was then mixed with two parts by weight of the titanium dioxide pigment. Balloon 22 is made from this formulation, and may be directly molded about and in contact with shaft 10.

Y-connector site 26 may be formulated out of the same material as it was formulated from in the previous example.

The distal end of catheter shaft 10 is inserted into an injection mold for Y-site 26, with the Y-site being then molded about the distal end, with good adhesion taking place between the molded Y-connector 26 and shaft 10 of the catheter without the need for an adhesive.

Valve 30 is then inserted into the Y-site to complete the construction of the catheter which exhibits the advantages described previously.

EXAMPLE 3

In this example, shaft 10 for a catheter was made from a formulation comprising 100 parts by weight of the following ingredients:

(a) 30 percent by weight of the block copolymer material utilized in the balloon formulation in Example 2 (Kraton 1662).

(b) 20 percent by weight of the poly(ethylene-butylene)-polystyrene copolymer of Example 1(b), and further containing an effective level of the Example 1. antioxidant described previously (Kraton G1650).

(c) 5 percent of the polypropylene formulation having a melt flow of 60 as described in Example 2.

(d) 5 percent by weight of a polypropylene material having a melt flow of about 2.

(e) 40 percent by weight of the mineral oil described in Example 1.

To 100 parts by weight of this mixture was added 2 parts by weight of the titanium dioxide pigment described previously. The mixture is processed as previously described.

It is also contemplated as an alternative to utilize a single type of antioxidant, either one or the other, in conjunction with the two types of block copolymer.

This material was blended and extruded in the manner of the previous examples to form shafts 10 of catheters made in accordance with this invention.

The balloon was extruded of the same material as in Example 2, and sealed onto the shaft, after punching aperture 20. The Y-connector site material may be identical to the shaft material of Example 1 and may be molded on to the shaft in the same manner as is described previously.

It is noted in this Example that, because of the relatively low average molecular weight and Brookfield viscosity of the block copolymer utilized herein, it is not necessary to provide a low melting polystyrene to the balloon or the shaft formulations since adhesion between the materials upon molding takes place spontaneously in this instance.

That which is claimed is:

1. A balloon-type catheter which comprises a tubular shaft and an inflatable balloon member, carried by said catheter, said shaft and balloon member being made of an elastic composition which comprises: at least 40 percent by weight of a block copolymer having thermoplastic rubber characteristics with a central block of ethylene-butylene copolymer and terminal blocks of polystyrene: from 0 to 45 percent by weight of polypropylene, at least one of said shaft and balloon member containing from 5 to 30 percent by weight of a tackifying agent comprising a low molecular weight polystyrene; said formulation being united with sufficient hydrophobic oil-type plasticizer to provide the desired degree of softness to said elastic composition.

2. The balloon-type catheter of claim 1 which carries a molded branched connector at its distal end attached to said tubular shank, said branched connector being made of said elastic composition.

3. The balloon-type catheter of claim 2 in which the formulation for said shaft contains from one to five percent by weight of polypropylene having a melt flow of essentially 50 to 100, as tested under ASTM D1238-70.

4. A balloon-type catheter which comprises a tubular shaft and an inflatable balloon member, carried by said catheter, said shaft and balloon member being made of an elastic composition which comprises: a block copolymer having thermoplastic rubber characteristics with a central rubbery polyolefin block and terminal blocks of polystyrene, said block copolymer exhibiting a Brookfield viscosity at 25 degrees C. of 10 to 2000 cps. when measured using a 10 percent by weight solids solution in toluene, said composition optionally including from 0 to 45 percent by weight of polypropylene, said formulation being mixed with sufficient hydrophobic oil-type plasticizer to provide the desired degree of softness to said elastic composition, said balloon member being sealed in position on said shaft.

5. The balloon-type catheter of claim 4 which carries a molded, branched connector at its distal end attached to said tubular shank, said branched connector being made of said elastic composition.

6. The balloon-type catheter of claim 5 in which the formulation for said shaft contains from one to five percent by weight of polypropylene having a melt flow of essentially 50 to 100, as tested under ASTM D1238-70.

7. The catheter of claim 6 which contains a titanium oxide pigment.

* * * * *

UNITED STATES PATENT OFFICE
CERTIFICATE OF CORRECTION

Patent No. 4,154,244    Dated May 15, 1979

Inventor(s) LAWRENCE F. BECKER, ET AL.

It is certified that error appears in the above-identified patent and that said Letters Patent are hereby corrected as shown below:

Add the following claims:

8. The catheter of Claim 4, in which said central rubbery polyolefin block is an ethylene-butylene copolymer.

9. The catheter of Claim 5, in which said central rubbery polyolefin block comprises from 50 to 85 percent by weight of the copolymer molecule.

10. The catheter of Claim 4, in which at least one of said shaft and balloon member contains from 5 to 30 percent by weight of a tackifying agent which comprises a low molecular weight polystyrene.

On the title page, after the "abstract", "7 claims" should read --- 10 Claims ---.

Signed and Sealed this

Twentieth Day of November 1979

[SEAL]

Attest:

RUTH C. MASON
Attesting Officer

LUTRELLE F. PARKER
Acting Commissioner of Patents and Trademarks